United States Patent [19]

Schmerling

[11] 4,005,126
[45] Jan. 25, 1977

[54] PREPARATION OF HALOALKYL ESTERS

[75] Inventor: Louis Schmerling, Riverside, Ill.

[73] Assignee: Universal Oil Products Company, Des Plaines, Ill.

[22] Filed: May 5, 1975

[21] Appl. No.: 574,494

[52] U.S. Cl. .................. 260/476 R; 260/410.9 R; 260/475 R; 260/485 H; 260/486 H; 260/496
[51] Int. Cl.$^2$ ........................................ C07C 67/24
[58] Field of Search ....... 260/485 H, 476 R, 475 R, 260/496, 486 H, 410.9 R

[56] References Cited

UNITED STATES PATENTS 2,513,504  7/1950  McFarlane .................. 260/476 R

*Primary Examiner*—Jane S. Myers
*Attorney, Agent, or Firm*—James R. Hoatson, Jr.; Raymond H. Nelson; William H. Page, II

[57]  ABSTRACT

Haloalkyl esters are prepared by converting a saturated cyclic ether to the desired product by reaction of said ether with a carboxylic acid and a hydrogen halide.

10 Claims, No Drawings

PREPARATION OF HALOALKYL ESTERS

BACKGROUND OF THE INVENTION

It has been known in the past that saturated cyclic ethers such as tetrahydrofuran or tetrahydropyran may be converted to esters by treatment with a carboxylic acid anhydride in the presence of certain catalytic compositions of matter. For example, it has been stated in the prior art that the opening of tetrahydrofuran and tetrahydropyran rings by reaction with acetic anhydride was accomplished readily only in the presence of zinc chloride at a reaction temperature of about 100° C. or more. Other prior art methods of accomplishing the opening of the rings employed catalysts such as boron trifluoride, sulfuric acid, etc. Likewise it has also been disclosed in the prior art that tetrahydrofuran undergoes no cleavage even after being heated under reflux for 5hours with stannic chloride or after being treated with acetic acid and stannic chloride at higher reaction temperatures. Acyl halides may also be employed to effect the ring cleavage of tetrahydrofuran or tetrahydropyran. However, a disadvantage in utilizing these compounds is that said compounds must be first prepared from the acid before being reacted with the cyclic ether. The preparation of these compounds usually entails the reaction of an inorganic halide such as phosphorous pentachloride and the desired acid. As will hereinafter be shown in greater detail, it has now been discovered that haloalkyl esters may be prepared by converting saturated cyclic ethers such as the tetrahydrofurans or tetrahydropyrans by reaction with a carboxylic acid or anhydride thereof and a hydrogen halide as such or in aqueous solution.

This invention relates to a process for the preparation of haloalkyl esters. More specifically, the invention is concerned with a proces for preparing haloalkyl esters by reacting a saturated cyclic ether with a carboxylic acid or anhydride thereof and a hydrogen halide in a non-catalytic process to prepare the desired compound.

Haloalkyl esters which may be prepared according to the process of this invention will find a wide variety of uses in the chemical field. For example, the aforementioned haloalkyl esters may be used as intermediates for the preparation of detergents or agents for decreasing the evaporation of water. For example, a haloalkyl ester such as 4-chlorobutyl acetate which has been prepared by reacting tetrahydrofuran with acetic acid and hydrochloric acid may be reacted with a long chain alkylaromatic compound such as n-octylbenzene to form a product which can be used as such or which may be converted to the sulfuric ester by treatment with sulfuric acid or to a non-ionic detergent in the form of a polyethylene ether via reaction with ethylene oxide.

It is therefore an object of this invention to provide a process for the preparation of haloalkyl esters.

A further object of this invention is to provide a process for preparing haloalkyl esters by reacting a carboxylic acid or anhydride thereof and a hydrogen halide or hydrohalic acid with a compound such as tetrahydropyran.

In one aspect an embodiment of this invention resides in a process for the preparation of a haloalkyl ester which comprises reacting a carboxylic acid or anhydride thereof and a hydrogen halide or hydrohalic acid with a saturated cyclic ether at reaction conditions, and recovering the resultant haloalkyl ester.

A specific embodiment of this invention is found in a process for the preparation of a halo ester which comprises reacting tetrahydrofuran with acetic acid and hydrochloric acid at a temperature in the range of from about ambient to about 100° C. and recovering the resultant 4-chlorobutyl acetate.

Other objects and embodiments will be found in the following further detailed description of the present invention.

As hereinbefore set forth, the present invention is concerned with a process for the preparation of haloalkyl esters by reacting a saturated cyclic ether with a carboxylic acid and a hydrogen halide at reaction conditions. Inasmuch as the prior art has taught that the ring opening of a saturated cyclic ether to form an ester thereof must be effected in the presence of a catalyst at relatively high temperatures, it was totally unexpected that this ring opening and formation of an ester by reacting a saturated cyclic ether with a carboxylic acid or anhydride thereof could be effected in a non-catalytic manner by utilizing a hydrogen halide as one of the reactants. In addition to being able to effect the reaction in a non-catalytic manner, it was also unexpected to find that the reaction would proceed at relatively low temperatures, that is, below about 100° C. and usually in a range of from about ambient (20°–25° C.) up to about 100° C.

Examples of saturated cyclic ethers which may be utilized as one of the starting materials in the process of this invention will include both 4 and 5 carbon-atom-membered rings, specific examples of these saturated ethers including tetrahydrofuran, tetrahydropyran, as well as alkyl- and halogen-substituted tetrahydrofurans and tetrahydropyrans in which the alkyl substituents may contain from 1 to about 6 carbon atoms such as 2-methyltetrahydrofuran, 2-ethyltetrahydrofuran, 2-propyltetrahydrofuran, 2-isopropyltetrahydrofuran, 2-n-butyltetrahydrofuran, 2-sec-butyltetrahydrofuran, 2-isobutyltetrahydrofuran, 2-t-butyltetrahydrofuran, 3-methyltetrahydrofuran, 3-ethyltetrahydrofuran, 3-propyltetrahydrofuran, 2-n-pentyltetrahydrofuran, 2-sec-pentyltetrahydrofurans, 2-n-hexyltetrahydrofuran, 2-sec-hexyltetrahydrofurans, 2-chlorotetrahydrofuran, 2-bromotetrahydrofuran, 2,3-dimethyltetrahydrofuran, 2,4-dimethyltetrahydrofuran, 2,5-dimethyltetrahydrofuran, 2,3-diethyltetrahydrofuran, 2,4-diethyltetrahydrofuran, 2,4-diisopropyltetrahydrofuran, 2,5-di-n-butyltetrahydrofuran, 2-methyltetrahydropyran, 2-ethyltetrahydropyran, 2-propyltetrahydropyran, 2-isopropyltetrahydropyran, 2-n-butyltetrahydropyran, 2-isobutyltetrahydropyran, 2-sec-butyltetrahydropyran, 3-methyltetrahydropyran, 3-ethyltetrahydropyran, 3-propyltetrahydropyran, 4-methyltetrahydropyran, 4-ethyltetrahydropyran, 4-propyltetrahydropyran, 2-n-pentyltetrahydropyran, 2-sec-pentyltetrahydropyran, 2-n-hexyltetrahydropyran, 2-sec-hexyltetrahydropyran, 2-chlorotetrahydropyran, 2-bromotetrahydropyran, 2,3-dimethyltetrahydropyran, 2,3-diethyltetrahydropyran, 2,4-dimethyltetrahydropyran, 2,4-diisopropyltetrahydropyran, 2,5-dimethyltetrahydropyrane, 2,6-dimethyltetrahydropyran, etc. It is to be understood that these saturated cyclic ethers are only representative of the class of compounds which may be employed as one of the reactants, and that the present invention is not necessarily limited thereto.

The aforementioned saturated cyclic ethers are reacted with carboxylic acids, said carboxylic acids containing from 1 to about 20 carbon atoms and which may be saturated, unsaturated, aromatic, monobasic or polybasic in nature. Specific examples of the acids whch may be reacted with the saturated cyclic ethers will include the aliphatic monobasic fatty acids such as formic acid, acetic acid, propionic acid, butyric acid, valeric acid, caproic acid, oenanthylic acid, caprylic acid, pelargonic acid, capric acid, undecylic acid, lauric acid, tridecoic acid, myristic acid, pentadecanoic acid, palmitic acid, margaric acid, stearic acid, nondecylic acid, arachidic acid, etc.; aromatic acids such as benzoic acid, o-toluic acid, m-toluic acid, p-toluic acid, phthalic acid, isophthalic acid, terephthalic acid, 2-phenylacetic acid, 3-phenylpropionic acid, 4-phenylbutyric acid, 5-phenylvaleric acid, etc; unsaturated monobasic acids such as the acrylic acid series including acrylic acid, crotonic acid, isocrotonic acid, tiglic acid, senecioic acid, hexenoic acid, teracrylic acid, oleic acid, etc.; aliphatic dibasic acids such as oxalic acid, malonic acid, succinic acid, glutaric acid, adipic acid, pimelic acid, suberic acid, azelaic acid, sebacic acid, etc.; unsaturated dibasic acids such as fumaric acid, maleic acid, glutaconic acid, citriconic acid, allylmalonic acid, allylsuccinic acid, etc. In addition to the aforementioned carboxylic acids, it is also contemplated within the scope of this invention that the anhydrides thereof may also be employed as one of the reactants in the reaction of the present invention, said anhydrides including acetic anhydride, propionic anhydride, butyric anhydride, etc.; phthalic anhydride, benzoic acid anhydride, acrylic acid anhydride, crotonic acid anhydride, tiglic acid anhydride, oxalic acid anhydride, malonic acid anhydride, succinic acid anhydride, etc.; maleic acid anhydride, glutaconic acid anhydride, etc. As in the case of the saturated cyclic ethers, the aforementioned carboxylic acids and anhydrides thereof are only representative of the class of compounds which may be employed and that the present invention is not necessarily limited thereto.

In addition to the aforementioned saturated cyclic ethers and carboxylic acids, the third component of the reaction will comprise a hydrogen halide, the preferred hydrogen halides being hydrogen chloride and hydrogen bromide due to the relatively greater availability and lower cost thereof. These hydrogen halides may be employed in either the anhydrous form as gases or as aqueous solutions, for example, hydrochloric acid or hydrobromic acid, etc.

The process of this invention may be effected in any suitable manner and may comprise either a batch or continuous type operation. For example, when a batch type operation is used and the hydrogen halide is in aqueous form, a desired quantity of each of the reactants, namely, the saturated cyclic ether, the carboxylic acid or anhydride thereof, and the aqueous hydrogen halide are placed in an appropriate apparatus which may comprise a reaction vessel provided with stirring means and, if so desired, heating means. The mixture of the reactants is then continuously stirred at a predetermined operating temperature which may range from ambient up to about 100° C. for a predetermined residence time which may range from about 0.5 up to about 10 hours or more in duration. Upon completion of this time period, the reaction mixture is recovered and subjected to conventional means of separation and purification such as washing, drying, extraction, fractional distillation, etc., whereby the desired haloalkyl ester is separated and recovered from any unreacted starting materials and/or side reaction products which may have been formed. In the event that the hydrogen halide which comprises one of the reactants of the present process is to be utilized in gaseous form, other types of appropriate apparatus such as autoclaves may be employed with equivalent results.

It is also contemplated within the scope of this invention that the process for the formation of haloalkyl esters may also be effected in a continuous manner of operation. When this type of operation is to be employed, the reactants comprising, as hereinbefore set forth, a saturated cyclic ether, a carboxylic acid or anhydride thereof and a hydrogen halide are continuously charged to a reaction vessel which is maintained at the appropriate operating temperature. The reactants may be charged to this reactor through separate lines or, if so desired, one or more may be admixed prior to entry into said reactor and the resulting mixture charged thereto in a single stream. Upon completion of the desired residence time, the reactor effluent is continuously withdrawn and subjected to the aforementioned conventional means of separation whereby the desired haloalkyl ester is separated and recovered while any unreacted starting materials may be recycled to form a portion of the feed stock.

The reactants may be present in the reaction zone in equimolar ratios although it is contemplated within the scope of this invention that the saturated cyclic ether may be present in an excess over the carboxylic acid or anhydride thereof and the hydrogen halide, the saturated cyclic ether being present in a mole ratio in the range of from about 1.1:1 to about 1.5:1 moles of saturated cyclic ether per mole of carboxylic acid or anhydride thereof and hydrogen halide.

The following examples are given for purposes of illustrating the process of the present invention. However, it is not intended that said invention be limited in strict accordance therewith.

EXAMPLE I

In this example a mixture consisting of 30 grams (0.05 mole) of acetic acid, 51 grams (0.72 mole) of tetrahydrofuran and 25 grams (0.26 moles) of concentrated hydrochloric acid was placed in a round-bottom flask and heated under reflux (85° C.) for 3.5 hours. At the end of this time, heating was discontinued and the reaction mixture was allowed to return to room temperature. The product was taken up in ether, water-washed, and the ether was evaporated on a steam bath. The residue (27 grams of water-white liquid) was shown by gas chromatography to consist chiefly to 4-chlorobutyl acetate together with a small amount of tetrahydrofuran.

EXAMPLE II

Fifty grams (0.69 mole) of tetrahydrofuran, 40 grams (0.40 mole) of acetic anhydride and 41 grams (0.43 mole) of concentrated hydrochloric acid were placed in an Erlenmeyer flask provided with heating and stirring means. The mixture was heated to a temperature of 40° C. and maintained thereat for a period of 1.5 hours, at the end of which time, heating was discontinued and the reaction mixture was recovered. It was treated like the product of Example I. There was recovered 26 grams of bottoms. gas chromatographic analysis of which disclosed that it consisted almost exclusively of 4-chlorobutyl acetate.

EXAMPLE III

In this example a mixture of 25 grams (0.26 mole) of concentrated hydrochloric acid and 60 grams (0.7 mole) of tetrahydropyran is placed in an Erlenmeyer flask and 39 grams (0.65 mole) of acetic acid is added thereto in a dropwise fashion, the temperature of the reaction being maintained in a range of from 70° to 75° C. The reaction is allowed to proceed at this temperature for a period of 4 hours, at the end of which time the reaction product if recovered and washed with water to remove any unreacted acetic acid and hydrochloric acid. The organic layer is separated from the aqueous layer, dried by passage over potassium carbonate and subjected to analysis by means of a gas chromatograph, said analysis disclosing that the major portion of the reaction product comprises 5-chloropentyl acetate.

EXAMPLE IV

To a mixture of 36 grams (0.5 mole) of tetrahydropyran and 42 grams (0.25 mole) of 48% hydrobromic acid is added dropwise 30 grams (0.4 mole) of propionic acid while maintaining the temperature of the solution in a range of from 60° to 65° C. Upon completion of the addition of the acid, the mixture is heated under reflux at 90° C. for a period of 3 hours. At the end of this time, heating is discontinued and the reaction mixture is allowed to return to room temperature. After taking up the reaction product in ether and washing with water to remove unreacted propionic acid and hydrobromic acid, the organic layer is recovered and subjected to gas chromatographic analysis, said analysis disclosing that a major portion of the product comprises 4-bromobutyl propionate.

EXAMPLE V

A mixture of 26 grams (0.26 mole) of concentrated hydrochloric acid and 61 grams (0.5 mole) of benzoic acid is placed in an Erlenmeyer flask provided with magnetic stirring means and heating means. Following this, 36 grams (0.5 mole) of tetrahydrofuran is slowly added to the mixture at 40° C. while subjecting said mixture to a constant stirring. The temperature of the reaction is raised to 100° C. and maintained thereat for a period of 4 hours, at the end of which time heating is discontinued and the reaction mixture allowed to return to room temperature. The reaction mixture is recovered and treated in a manner similar to that hereinbefore set forth whereby the reaction product is separated from any unreacted benzoic acid and hydrochloric acid. Analysis of the reaction product will disclose the fact that the major portion of said product comprises 4-chlorobutyl benzoate.

EXAMPLE VI

In like manner, a mixture of 43 grams (0.5 mole) of tetrahydropyran and 25 grams (0.26 mole) of concentrated hydrochloric acid is placed in a reaction flask to which is added 46.5 grams (0.4 mole) of caproic acid. The mixture is then heated to a temperature of 60° C. and maintained thereat for a period of 4 hours, at the end of which time heating is discontinued and the reaction mixture is treated in a manner similar to that set forth in the above examples. After recovery of the reaction product, it is subjected to chromatographic analysis, said analysis disclosing that the major portion of the product comprises 5-chloropentyl caproate.

I claim as my invention:

1. A process for the preparation of a haloalkyl ester which comprises reacting, at a temperature of from about ambient to about 100° C., a hydrocarbon carboxylic acid containing from 1 to about 20 carbon atoms or anhydride thereof and a hydrogen halide or hydrohalic acid with a saturated cyclic ether selected from the group consisting of tetrahydrofuran, tetrahydropyran, halogen-substituted tetrahydrofurans and tetrahydropyrans and alkyl-substituted tetrahydrofurans and tetrahydropyrans in which the alkyl contains from 1 to about 6 carbon atoms, and recovering the resultant haloalkyl ester 2. The process as set forth in claim 1 in which said saturated cyclic ether is tetrahydrofuran.

3. The process as set forth in claim 1 in which said saturated cyclic ether is tetrahydropyran.

4. The process as set forth in claim 1 in which said hydrogen halide is hydrochloric acid.

5. The process as set forth in claim 1 in which said hydrogen halide is hydrobromic acid.

6. The process as set forth in claim 1 in which said carboxylic acid is acetic acid, said hydrogen halide is hydrochloric acid, said saturated cyclic ether is tetrahydrofuran and said haloalkyl ester is 4-chlorobutyl acetate.

7. The process as set forth in claim 1 in which said carboxylic acid is acetic acid, said hydrogen halide is hydrochloric acid, said saturated cyclic ether is tetrahydropyran and said haloalkyl ester is 5-chloropentyl acetate.

8. The process as set forth in claim 1 in which said carboxylic acid is propionic acid, said hydrogen halide is hydrobromic acid, said saturated cyclic ether is tetrahydrofuran and said haloalkyl ester is 4-bromobutyl propionate.

9. The process as set forth in claim 1 in which said carboxylic acid is benzoic acid, said hydrogen halide is hydrochloric acid, said saturated cyclic ether is tetrahydrofuran and said haloalkyl ester is 4-chlorobutyl benzoate.

10. The process as set forth in claim 1 in which said carboxylic acid is caproic acid, said hydrogen halide is hydrochloric acid, said saturated cyclic ether is tetrahydropyran and said haloalkyl ester is 5-chloropentyl caproate.

* * * * *